(12) United States Patent
Wilken

(10) Patent No.: US 8,927,619 B2
(45) Date of Patent: Jan. 6, 2015

(54) COLOR-STABILIZED IODOPROPYNYL BUTYLCARBAMATE

(71) Applicant: Jorg Thomas Wilken, Hannover (DE)

(72) Inventor: Jorg Thomas Wilken, Hannover (DE)

( * ) Notice: Subject to any disclaimer, the term of this patent is extended or adjusted under 35 U.S.C. 154(b) by 50 days.

(21) Appl. No.: 13/716,189

(22) Filed: Dec. 16, 2012

(65) Prior Publication Data

US 2013/0197127 A1 Aug. 1, 2013

Related U.S. Application Data

(60) Provisional application No. 61/578,795, filed on Dec. 21, 2011.

(51) Int. Cl.
| | | |
|---|---|---|
| *C09D 5/00* | (2006.01) | |
| *C07D 203/06* | (2006.01) | |
| *C09D 7/12* | (2006.01) | |
| *A01N 47/12* | (2006.01) | |
| *C09D 5/14* | (2006.01) | |

(52) U.S. Cl.
CPC .............. *C09D 7/1291* (2013.01); *A01N 47/12* (2013.01); *C09D 5/14* (2013.01); *C09D 7/1241* (2013.01)
USPC .......................................... 523/122; 428/402

(58) Field of Classification Search
CPC ........ A01N 47/12; C09D 5/14; C09D 7/1241; C09D 7/1291
USPC .......................................... 523/122; 428/402
See application file for complete search history.

(56) References Cited

U.S. PATENT DOCUMENTS

| | | | |
|---|---|---|---|
| 3,737,337 A | 6/1973 | Schnoring | |
| 4,794,130 A | 12/1988 | Hayakawa | |
| 5,846,554 A | 12/1998 | Scher | |
| 6,353,021 B1 | 3/2002 | Gaglani | |
| 6,506,794 B1 | 1/2003 | Yates | |
| 6,777,002 B1 | 8/2004 | Vuaridel | |
| 6,899,898 B2 | 5/2005 | Albayrak | |
| 7,252,842 B2 | 8/2007 | Albayrak | |
| 2009/0036555 A1 | 2/2009 | Uhr | |
| 2010/0051554 A1 | 3/2010 | Ahn | |
| 2011/0009268 A1 | 1/2011 | Uhr | |
| 2011/0274763 A1 * | 11/2011 | Nyden et al. .................. | 424/497 |
| 2012/0309897 A1 * | 12/2012 | Boettcher ..................... | 524/728 |

FOREIGN PATENT DOCUMENTS

WO    2012076699 A1    6/2012

OTHER PUBLICATIONS

PCT International Search Report and Written Opinion mailed Dec. 2, 2013 for PCT Patent Application PCT/US2013/042939, which claims prioirity from the present U.S. Appl. No. 13/716,189.

\* cited by examiner

*Primary Examiner* — Nathan M Nutter
(74) *Attorney, Agent, or Firm* — Robert A. Yesukevich

(57) ABSTRACT

Microparticles containing an ultraviolet light absorbing polymer and 3-iodo-2-propynyl butylcarbamate ("IPBC") resist discoloration by sunlight and other ultraviolet light sources. Methods for preparing the microparticles produce polymer-shielded, formaldehyde-free IPBC formulations which resist discoloration and leaching, and are especially useful in water-based applications. The microparticles include a polymer that absorbs light over a range of ultraviolet wavelengths associated with IPBC discoloration. The microparticles may be utilized in paints, stains, stuccoes, adhesives, and plastics, for example.

28 Claims, No Drawings

COLOR-STABILIZED IODOPROPYNYL BUTYLCARBAMATE

CROSS-REFERENCE TO RELATED APPLICATIONS

This application claims priority of a provisional application entitled "COLOR-STABILIZED IODOPROPYNYL BUTYLCARBAMATE", which is Application No. 61/578,795, filed Dec. 21, 2012, and is herein incorporated by reference in its entirety.

BACKGROUND OF THE INVENTION

1. Field of the Invention

The present invention relates to color-stabilized compositions which comprise a halopropynyl compound, such as 3-iodo-2-propynyl butylcarbamate (hereinafter referred to as "IPBC"), and to methods for making and using the compositions.

2. Description of the Related Art

Iodopropynyl carbamates are widely employed as preservatives in coating compositions. In particular, 3-iodo-2-propynyl butylcarbamate (hereinafter referred to as "IPBC") has achieved worldwide commercial success. IPBC was first disclosed and claimed in U.S. Pat. No. 3,923,870, issued to William Singer on Dec. 2, 1975 and assigned to the assignee of the present patent application.

While IPBC offers many advantages over other biocides, it is prone to a visually-detectable discoloration that is reportedly initiated or accelerated by exposure to sunlight or other ultraviolet light sources. Although light-related discoloration of IPBC-containing products is only sporadically encountered, and sometimes disappears after a period of weeks, it is of major concern to coating manufacturers. Because elemental iodine is yellow to brown, and because the tri-iodide anion ($I_3^-$) is a deep yellowish-brown color, some previous researchers have speculated that light-related discoloration of IPBC is accompanied by the formation of elemental iodine or other free radical fragments.

U.S. Pat. No. 4,276,211, issued to William Singer et al. on Jun. 30, 1981 and assigned to the assignee of the present application, describes the use of epoxides as color stabilizers for iodoalkynyl carbamate fungicides in paint compositions and coatings. U.S. Pat. No. 4,276,211 patent is hereby incorporated by reference in its entirety, and specifically for its teachings regarding stabilizers for IPBC.

U.S. Pat. No. 4,297,258, issued to Long, Jr., describes the use of epoxy-based acid scavengers to reduce IPBC yellowing or discoloration.

As another example, U.S. Pat. No. 5,554,784, issued to Gruening, describes a method for preparing IPBC that reportedly minimizes discoloration or yellowing in coating compositions exposed to sunlight.

Some previous researchers have suggested adding an ultraviolet absorber or a light stabilizer to IPBC to prevent or retard discoloration. For example, U.S. Pat. No. 6,472,424 B1, issued to Gaglani et al. and assigned to the assignee of the present application, describes benzylidene camphor as an IPBC stabilizer. Also, see U.S. Pat. No. 6,353,021 and U.S. Pat. No. 5,938,825, both issued to Gaglani et al., and assigned to the assignee of the present application, for recommendations regarding other IPBC stabilizers. U.S. Pat. Nos. 6,472,424 B1; 6,353,0212; and 5,938,825 are hereby incorporated by reference in their entirety, and specifically for their teachings regarding stabilizers for IPBC.

Other researchers favor absorbing, impregnating, or encapsulating IPBC within or on various solid carrier materials. For example, published WIPO patent application WO 2010/147820 A1 describes a stabilized biocidal dispersion comprising a biocide coated or adsorbed onto stable sub-micron carrier particles selected from metal oxides such as zinc oxide, titanium dioxide, cerium dioxide, and the like. As another example, U.S. Pat. No. 7,429,392 B2, issued to Baum et al., describes a coating material characterized in that it contains a biocide which bonds to solid particles in a carrier material and is released in a delayed manner. U.S. Pat. No. 7,429,392 B2 patent is hereby incorporated by reference in its entirety, and specifically for its teachings regarding biocides which are released from solid particles in a delayed manner.

Published patent application WO 2010/133548 A2 describes a production method for the preparation of small polymer microcapsules with an oil core and solid microspheres, comprising high amounts of biocide by internal phase separation from emulsion droplets with ethyl acetate as a solvent. Reportedly, the size of the microcapsules and microspheres can be controlled with a high degree of accuracy between 0.2-20 microns in diameter and the microparticles are well suited for protecting coatings.

Published patent application WO/2010/148158 A1 describes a process for the preparation of a sustained-release biocidal composition containing microencapsulated biocide, which comprises the steps of: (i) adsorbing the biocide onto an inert carrier and grinding to attain a desired particle size with a ratio of biocide to inert carrier in the range of about 1:99 to about 99:1; (ii) optionally coating the biocide and inert carrier with an appropriate amine or imine compound or a water resistant film forming polymer, and dispersing the encapsulated biocide in an aqueous medium in the presence of a dispersing agent; (iii) adding at least one thickening agent to re-disperse the encapsulated biocide; and (iv) preparing an aqueous or solvent based sustained release biocide dispersion.

Despite the impressive achievements of previous researchers over a period spanning thirty years, a need still exits for an IPBC composition that resists discoloration in end-use coatings formulations.

BRIEF SUMMARY OF THE INVENTION

It has now been discovered that certain microparticles containing an ultraviolet light absorbing polymer and IPBC resist discoloration by sunlight and other ultraviolet light sources. In addition, efficient methods for preparing the microparticles have been identified.

In one aspect, the invention is microparticles for stabilizing IPBC against discoloration. The microparticles include a polymer that absorbs light over a range of ultraviolet wavelengths associated with 3-iodo-2-propynyl butylcarbamate discoloration; 3-iodo-2-propynyl butylcarbamate; and, optionally, an additional biocidal material. The microparticles have a particle size in the range of more than 20 to about 1000 microns and a surface area in the range of about 0.001 to about 0.9 $m^2$ per gram. The microparticles stabilize 3-iodo-2-propynyl butylcarbamate against discoloration.

The polymer preferably has an absorbance that is 0.03 or greater at all wavelengths in the range of about 290 to about 380 nanometers. More specifically, the polymer preferably has an absorbance that is 0.03 or greater; and more preferably, 0.05 or greater at all wavelengths in the range of about 295 to about 320 nanometers. Absorbance is measured in liquid solution at a polymer concentration of 0.1 weight percent or less.

Preferably, the polymer is selected from the group consisting of poly(methyl methacrylate) ("PMMA"), poly(ethyl methacrylate) ("PEMA"), polyvinyl acetate ("PVAC"), polystyrene ("PS"), polycarbonate ("PC") and mixtures thereof.

In another aspect, the invention is a method for making microparticles for stabilizing IPBC. The method includes blending IPBC, an aqueous liquid phase, and an organic liquid phase. Preferably, particles of a partitioning agent are dissolved in the aqueous phase as a colloid in an amount effective to inhibit agglomeration of IPBC.

The organic phase includes a solvent selected from the group consisting of ethyl acetate, 2-methyl-(tetrahydro)-furane, dichloromethane, and mixtures thereof and a polymeric material that is present in the organic phase. Preferably, the polymeric material is composed of PMMA, PEMA, polyvinyl acetate, polystyrene, polycarbonate or mixtures thereof.

Preferably, the organic phase additionally includes a water-miscible co-solvent selected from the group consisting of acetone, methanol, and mixtures thereof. During the blending, IPBC and/or the polymer may be present as solid particles in the aqueous phase and/or as solid particles or as a solute in the organic liquid phase. The blending produces a mixture.

The mixture is stirred under conditions effective for extracting the organic solvent at least partially into the aqueous liquid phase, without evaporation of the organic solvent. Under these conditions at least a portion of the polymeric material separates from the organic phase and hardens to form microparticles including polymer material and IPBC. Preferably, the separation mixture is stirred at a temperature in the range of about 20 to about 50 degrees C. while the polymeric material separates from the organic phase. More preferably, these conditions also include lowering the temperature of the separation mixture, adding water to the separation mixture, adding inorganic salts to increase the ionic strength of the aqueous phase, and/or adding an emulsion breaker to the separation mixture to promote separation and deposition of the polymeric material.

DETAILED DESCRIPTION OF PREFERRED EMBODIMENTS

The invention provides microparticles including an ultraviolet light absorbing polymer and IPBC, which resist discoloration by sunlight and other ultraviolet light sources. The invention also provides methods for preparing the microparticles. The methods may be operated at relatively low-temperature in a single reaction vessel. The methods avoid any need to form a stable emulsion or to evaporate solvent in order to initiate polymer deposition or formation of the microparticles.

In a preferred embodiment, the invention is microparticles for stabilizing 3-iodo-2-propynyl butylcarbamate against discoloration. The microparticles include a polymer and IPBC. The microparticles have a particle size in the range of more than 20 to about 1000 microns. The surface area of the microparticles is preferably in the range of about 0.001 to about 0.9 $m^2$ per gram, more preferably about 0.01 to about 0.7 $m^2$ per gram, and most preferably about 0.1 to about 0.5 $m^2$ per gram. The polymer absorbs light over a range of ultraviolet wavelengths associated with IPBC discoloration. Optionally, one or more biocides are included in the microparticles.

For the present purposes, the "size" of a microparticle means the greatest linear dimension of the microparticle. Preferably, each of the microparticles of the invention has a size in the range of more than 20 to about 1000 microns; more preferably, more than 30 to about 800 microns; most preferably, more than 40 to about 500 microns; ideally, more than 50 to about 100 microns. Surprisingly, there appears to be an anomalous size range in which microparticles provide relatively little stabilization against discoloration for IPBC.

"Volume-average particle diameter" and "average particle size" are intended to be synonyms for the purposes of the present application. Preferably, the microparticles have an average particle size in the range of about 20 about 1000 microns; more preferably, about 30 to about 800 microns; most preferably, about 40 to about 500 microns; ideally, about 50 to about 100 microns.

For the present purposes, "absorbance" means $\log_{10}(I_0/I)$, where I is the intensity of light at a specified wavelength that has passed through a sample in the form of a liquid solution having a concentration of 0.1 weight percent or less and $T_0$ is the intensity of the light before it enters the sample. For example, a spectrometer for measuring absorbance is commercially available from Shimadzu Corporation of Kyoto, Japan under the tradename UV-2401PC.

IPBC discoloration is associated with irradiation by light having a wavelength of about 290 nanometers to about 380 nanometers. IPBC is known to absorb ultraviolet light in wavelengths over a range of 190 to 320 nanometers, and to exhibit absorption maxima at about 190 and about 230 nanometers. In addition, IPBC discoloration has been reported upon exposure to natural sunlight. The shortest wavelength normally found in sunlight at the earth's surface is about 295 nanometers.

Preferably, the polymer exhibits absorbance that is 0.03 or greater, more preferably, 0.05 or greater; most preferably 0.08 or greater; and ideally 0.10 or greater at all wavelengths in the range of about 290 to about 380 nanometers, more specifically in the range of about 290 to about 350 nanometers.

Also, it is preferred that the polymer exhibits absorbance that is 0.03 or greater, more preferred, 0.05 or greater; most preferred, 0.0.08; and ideally, 0.10 or greater at all wavelengths in the range of 295 to 320 nanometers.

It is also preferred that the polymer exhibits absorbance of less than 0.10, and especially preferred that the polymer exhibits absorbance of less than 0.05, at all wavelengths in the range of about 400 to about 740 nanometers. Ideally, the polymer appears colorless to the human eye. For the present purposes, "colorless" means white or transparent.

While not intending to be bound by theory, it is believed that by absorbing ultraviolet light that would otherwise impinge on IPBC, the polymer prevents or retards discoloration of IPBC and, thereby, stabilizes IPBC located within or on the polymer against discoloration.

The polymer may be, for example, PMMA, PEMA, polyvinyl acetate, polystyrene, polycarbonate and mixtures thereof. As another example, the polymer may be selected from the group consisting of PMMA, PEMA, polyvinyl acetate, polystyrene, polycarbonate, and copolymers thereof.

Practitioners in the field of the polymer chemistry will understand how to select, manufacture, or blend particular polymers or particular polymer mixtures that provide desired absorbance over the various wavelength ranges described above. Preferably, the polymer is selected from the group of PMMA or PMEA and mixtures thereof. More preferably, the polymer is PMMA.

Formaldehyde-free polymeric materials are preferred for use as the polymer in microparticles of the present invention. Polymeric materials that include a significant amount of formaldehyde are not suitable for use in the present invention. For example, melamine formaldehyde generally contains formaldehyde in amounts that appear to cause discoloration of IPBC.

Preferably, the polymer has a molecular mass in the range of about 15,000 to about 1,000,000 g/mol. For example, the polymer may be PMMA or PEMA with a molecular mass in the range of about 40,000 to about 700,000 g/mol; the polymer may be polyvinyl acetate with a molecular mass in the range of about 40,000 to about 700,000 g/mol; the polymer may be polystyrene with a molecular mass in the range of about 15,000 to about 500,000 g/mol; the polymer may be a polycarbonate with a molecular mass in the range of about 10,000 to about 300,000 g/mol; or the polymer may be a mixture of any or all of these. It is contemplated that the polymer may be a copolymer of two or more of PMMA, PEMA, polyvinyl acetate, polystyrene, and polycarbonate.

In the microparticles, the weight ratio of IPBC to the polymer is preferably in the range of about 0.01:1 to about 9:1; more preferably, in the range of about 0.1:1 to about 2:1; most preferably, in the range of about 0.2:1 to about 1:1.

The microparticles may be dispersed in a liquid carrier phase for use. For example, the microparticles of the invention dispersed in water would be very suitable for use as a preservative in water-based paint or water-based stucco. The microparticles of the invention could also be suitable for use in solvent-based paints, stains or wood preservatives, among other things.

Other biocides, in addition to IPBC, may optionally be located within or on the polymer of the invention. For example, additional biocides selected from the group consisting of isoproturon; Terbutryn; 3-(3,4-dichlorophenyl)-1,1-dimethylurea; N-cyclopropyl-N'-(1,1-dimethylethyl)-6-(methylthio)-1,3,5-triazine-2,4-diamine carbendazim; zinc pyrithione; 4,5-dichloro-2-n-octyl-3-isothiazolone; 2-n-octyl-4-isothiazolin-3-one; and mixtures thereof may be included in the microparticles. Preferably, the additional biocide is isoproturon. More preferably, the additional biocide is Terbutryn.

In another embodiment, the invention is a method for making liquid-dispersible microparticles that include IPBC and, optionally, an additional biocide or a stabilizing agent. The method involves preparing or providing a suspension or dispersion that includes IPBC particles dispersed in an aqueous continuous phase. A partitioning agent, preferably in the form of a colloid, may be present in the continuous phase to inhibit agglomeration of the IPBC particles with each other. Polyvinyl alcohol ("PVA") is a preferred partitioning agent, more preferred when it is about 87 to about 95% hydrolyzed, and most preferred when it is about 87 to about 89% hydrolyzed. Good results have been obtained when the partitioning agent has a molecular mass in the range of about 13,000 to about 23,000 g/mol.

The method also involves preparing or providing an organic liquid phase which includes a solvent that is sparingly water-soluble, preferably having a solubility in water at room temperature in the range of about 100 to about 1000 ppm. Preferably, the sparingly soluble solvent is selected from the group consisting of ethyl acetate, 2-methyl-(tetrahydro)-furane, dichloromethane, and mixtures thereof. The organic phase also includes a polymeric material, such as poly(methyl methacrylate), poly(ethyl methacrylate), polyvinyl acetate, polystyrene, polycarbonate, or mixtures thereof. Poly(methyl methacrylate) ("PMMA") is preferred for use as the polymeric material. The sparingly water-soluble solvent must be capable of dissolving a significant proportion of the polymeric material at temperatures of about room temperature to about 50 degrees C. Optionally, a water miscible co-solvent, such as acetone or methanol, may be incorporated in the organic liquid phase in addition to the sparingly water-soluble solvent.

The method for making microparticles of the invention includes blending the aqueous suspension or dispersion with the organic phase under separation conditions effective for extracting the organic solvent at least partially into the continuous phase of the aqueous suspension or dispersion in a controlled manner. The separation conditions include mixing or otherwise agitating the separation mixture under atmospheric pressure at a temperature that is equal to or warmer than room temperature and cooler than the melting temperature of IPBC. Preferably, the separation temperature is in the range of about 20° C. to about 50° C. Blending the aqueous suspension with the organic phase at the separating conditions produces a phase separation mixture.

As the separation mixture is stirred or otherwise agitated under the separation conditions, at least a portion of the polymeric material separates from the organic phase to form microparticles that include the polymeric material, and include IPBC located within or on the polymeric material, and hardens. Preferably, the polymeric material separates from the organic phase and associates with the IPBC particles within seconds or a few minutes. The rate of separation and association depends on process parameters such as stirring rate, addition rate, temperature, the amount of water and solvents present in the separation mixture, and the presence of co-solvents such as water miscible solvents, solvent extraction fluids, and inorganic salts.

For the present purposes, "associates with" means absorbs, adsorbs, imbibes, surrounds, chelates, adheres, or binds.

While not intending to be bound by theory, it is believed that the separation-and-association phenomenon is induced by diffusion of the sparingly soluble solvent into the continuous phase of the aqueous suspension. If present, co-solvents such as acetone or methanol would be expected to diffuse in the same direction. The microparticles produced by the present invention exhibit a degree of smoothness and uniformity which indicates that the polymeric material separates from the organic phase via a short term formation of a viscous liquid phase, rather than a solid precipitate.

In order to promote further separation of the polymeric material from the organic phase and further hardening of the microparticle walls, the separation-and-association phenomenon, may optionally be followed by cooling the separation mixture to room temperature and/or adding water to the separation mixture. A similar effect may be achieved by adding inorganic salts (such as sodium sulfate, sodium chloride, or calcium chloride) to the continuous phase of the aqueous suspension.

After the microparticles have hardened sufficiently, the microparticles may be recovered from the separation mixture by removal of the liquid contents via, for example, centrifugation or filtration. Various components of the organic phase and the aqueous suspension may be recycled by known processes.

The polymer separation with IPBC association process is completed by lowering the mixing temperature to room temperature and by adding additional water. Increasing the ionic strength of the aqueous phase ("salting out") with inorganic salts (sodium sulfate, sodium chloride, etc.) or the addition of a solvent-extracting, third solvent with non-solvent properties for the polymer are other approaches to complete the polymer deposition step.

In yet another embodiment, the invention is a method for reducing IPBC discoloration in a dry film or coating, such as paint or stucco. The method includes microparticles of the invention that provide polymer-shielding of a biocidal composition that includes IPBC and a stabilizing agent, such as a Hindered Amine Light Stabilizer ("HALS") and/or a UV absorber ("UVA"), before the IPBC is incorporated in the dry film or coating. Preferably, the weight ratio of IPBC to UVA or of IPBC to HALS in the microparticles is in the range of about 19:1 to about 2.3:1; more preferably in the range of about 9:1 to about 7:1.

Preferably, the biocidal composition includes the free radical scavenger, and the free radical scavenger is a hindered amine light stabilizer. Preferably, the biocidal composition includes the ultra-violet absorber, and the ultra-violet absorber is a benzotriazole or a benzophenone. It is also preferred that the weight ratio of polymeric material to the biocidal composition in the microparticles is in the range of about 9:1 to about 1:9.

The preparation of the polymer-shielded IPBC microparticles is not limited to a particular manufacturing procedure. Described herein is just one of many procedures for preparing the polymer-shielded IPBC particles. Preferably, IPBC and the stabilizing agent are combined with a polymer and incorporated into a microparticle according to the phase separation method for making microparticles described above.

As described below, the preparation of PMMA-shielded IPBC microparticles can be achieved—with equally good performance results in terms of non-yellowing properties and leaching resistance—by:

i) starting from an aqueous IPBC suspension containing IPBC crystalline particles, or ii) starting from an aqueous dispersion containing IPBC particles, or iii) starting from IPBC dissolved alone or with a polymer material in organic solvent(s).

A one-step process of phase separation or precipitation of IPBC with or onto an ultraviolet light absorbing polymer (or mixtures of ultraviolet light absorbing polymers) from an organic phase leads to the formation of polymer-shielded IPBC microparticles. Microparticles of the invention can be prepared (in accordance with the processes described below) in many sizes ranging from about 0.1 microns to upwards of 1000 microns. The size produced depends, for example, on parameters such as stirring speed, solvent volume, temperature, and concentration of polymer(s), among others. With the benefit of teaching set forth above and specific examples below, the appropriate combination of process parameters will be apparent to experienced practitioners in the art of microparticle manufacturing.

EXPERIMENTAL

The following examples and procedures are presented to better communicate the invention, and are not meant to limit the invention in any way. Unless otherwise indicated, all references to parts, percentages or proportions are based on weight.

UV Discoloration Test Procedure

In order to quantify discoloration of various materials in the presence of ultraviolet light, a test box equipped with ultraviolet lamps of a type commercially available under the tradename UVA-340 from Q-Panel Lab Products, Cleveland, Ohio 44145 U.S.A. is utilized. The lamps are fluorescent and rated for 40 watts of electrical power, with an emission range of 280 to 350 nanometers and a continuous peak output at 310 nanometers.

UV Discoloration Tests are performed in the test box on particular materials of interest that are incorporated by mixing for five minutes into wet Stolit® K2 stucco to prepare test specimens. The stucco is commercially available from Sto AG of Stühlingen, Germany. The test specimens contain IPBC at a use level of 1000 ppm, with a thickness of about 2 mm, on substrate panels which are commercially available from Leneta Company, Inc. of Mahwah, N.J. U.S.A.

The test specimens are dried for approximately 12 hours at 22° C. The dried test specimens are exposed to ultraviolet light in the test box with all four lamps illuminated for a test period of four, six or eight hours. A temperature of 40-42° C. is continuously maintained in the test box throughout the test period.

CIEL*a*b* colorimetry values, which use b* as the criteria for yellowness, are measured from the surface of each test specimen. "Delta b" means the absolute value of the numerical difference in b* value of the test specimen before and after a test period. Greater delta b indicates more discoloration, and 0.0 delta b is indicative of no discoloration. It is noteworthy that delta b of less than 2.0 is difficult to detect by the human eye. In most cases, an average delta-b value calculated as the mean average of more than one discoloration test is reported.

Preparative Example A

Inventive Process for Making Microparticles

The following ingredients are assembled in the following amounts:

| Ingredient | grams | wt % |
| --- | --- | --- |
| Poly(methyl methacrylate) - MW 350,000 | 4.90 | 1.74 |
| Ethyl acetate | 49.57 | 17.65 |
| IPBC crystalline particles, milled to <40 microns (contains 98% IPBC) | 1.63 | 0.58 |
| Acetone (optional) | 2.35 | 0.84 |
| De-ionized water | 220.00 | 78.34 |
| Poly(vinyl alcohol), MW 13,000-23,000; 87-89% hydrolyzed | 2.40 | 0.85 |

A dispersion is prepared by placing 120 g of de-ionized water in a metal beaker at 50° C. and adding, with stirring by a 60 mm dissolver disk/blade at 900 revolutions per minute, 2.40 grams of polyvinyl alcohol that has a molecular mass in the range of 13,000 to 23,000 g/mol and is 87-89% hydrolyzed. The metal beaker is a double-walled metal beaker of 80 millimeters interior diameter and 500 ml capacity, combined with a programmable thermostat. To the colloidal dispersion is added 1.63 g of crystalline IPBC particles, having a maximum particle size of less than 40 microns, to produce an aqueous suspension.

An organic liquid phase is prepared by placing 49.57 grams of ethyl acetate in a round-bottom flask and heating to 50° C. PMMA in the amount of 4.90 grams is added to the ethyl acetate and the mixture is stirred while the PMMA is completely dissolved. Acetone in the amount of 2.35 grams is also introduced into the organic liquid phase at this point. An UV absorber and/or a HALS may optionally be added to either of the liquid phases, preferably added to the organic liquid phase.

The organic liquid phase is blended with the aqueous suspension in the metal beaker by stirring at 900-1200 revolutions per minute for 60 minutes at 50 degrees C. Microparticles encasing IPBC are produced. The microparticles are composed of about 25 wt % IPBC and about 75 wt % PMMA.

The contents of the metal beaker are cooled to room temperature over a period of thirty minutes. Water in the amount of 100 grams is added to the metal beaker. The microparticles are separated from the balance of the metal beaker contents by filtration, are washed with de-ionized water and are dried. Approximately 6.5 grams of microparticles are recovered.

Preparative Example B

Inventive Process for Making Microparticles

The following raw ingredients are assembled in the following amounts:

| Ingredient | grams | wt % |
|---|---|---|
| Poly(methyl methacrylate) - MW 350,000 | 4.90 | 1.73 |
| Ethyl acetate | 49.57 | 17.50 |
| IPBC aqueous dispersion (contains 40% IPBC) | 4.06 | 1.43 |
| Acetone (optional) | 2.35 | 0.83 |
| De-ionized water | 220.00 | 77.66 |
| Poly(vinyl alcohol) - MW 13,000-23,000, 87-89% hydrolyzed | 2.40 | 0.85 |

The procedure described above in Preparative Example A is performed, except that a) 4.06 grams of a 40% aqueous dispersion containing 1.63 g of IPBC particles is added to the aqueous phase, rather than employing 1.63 grams of pre-milled IPBC crystalline particles; and b) the organic phase is blended with the dispersion by stirring at about 900-1200 or alternatively at about 2800 revolutions per minute; and c) a defoamer may optionally be added during this stirring; and d) in addition an UV absorber and/or a HALS may optionally be added.

It is observed that at a stirring rate of about 2800 rpm more than 80% of the recovered microparticles are significantly smaller than 100 microns.

Preparative Example C

Inventive Process for Making Microparticles

The following raw ingredients are assembled in the following amounts:

| Ingredient | grams | wt % |
|---|---|---|
| Poly(methyl methacrylate) - MW 350,000 | 4.90 | 1.74 |
| Ethyl acetate | 49.57 | 17.65 |
| IPBC crystalline particles (contains >98% IPBC) | 1.63 | 0.58 |
| Acetone (optional) | 2.35 | 0.84 |
| De-ionized water | 220.00 | 78.34 |
| Poly(vinyl alcohol) - MW 13,000-23,000, 87-89% hydrolyzed | 2.40 | 0.85 |

The procedure described above in Preparative Example A is performed, except that a) 1.63 g of IPBC particles are dissolved together with the PMMA polymer in the organic liquid phase, rather than suspended in the aqueous liquid phase; b) a defoamer may optionally be added during this stirring; and c) an UV absorber and/or a HALS may optionally be added to the organic liquid phase.

Preparative Example D

Inventive Process for Making Microparticles

The following raw ingredients are assembled in the following amounts:

| Ingredient | grams | wt % |
|---|---|---|
| Poly(methyl methacrylate) - MW 350,000 | 4.90 | 2.12 |
| Ethyl acetate | 49.57 | 21.43 |
| IPBC crystalline particles (contains >98% IPBC) | 1.63 | 0.70 |
| Calcium chloride | 0.50 | 0.22 |
| Acetone (optional) | 2.35 | 1.02 |
| De-ionized water | 170.00 | 73.48 |
| Poly(vinyl alcohol) - MW 13,000-23,000, 87-89% hydrolyzed | 2.40 | 1.03 |

The procedure described above in Example C is performed, except that a) the mixture is stirred with a Ultraturaxx high-performance disperser from IKA® (IKA-Werke GmbH & Co. KG, Germany) at 3400 revolutions per minute, rather than stirring with a dissolver disk at about 900-1200 rpm; b) 0.50 g calcium chloride is added to the aqueous phase as an emulsion breaker; c) a small amount of a defoamer may optionally be added to the mixture; and d) a UV absorber and/or a HALS may optionally be added preferably to the organic liquid phase.

It is observed that more than 95% of the recovered microparticles are significantly smaller than 25 microns.

Preparative Example E

Inventive Process for Making Microparticles

The following ingredients are assembled in the following amounts:

| Ingredient | grams | wt % |
|---|---|---|
| Poly(methyl methacrylate) - MW 447,000 | 4.80 | 1.80 |
| Ethyl acetate | 36.90 | 13.85 |
| IPBC crystalline particles (contains >98% IPBC) | 1.60 | 0.60 |
| Acetone (optional) | 0.70 | 0.26 |
| Deionized water | 219.8 | 82.50 |
| Kelzan CC (as solute in de-ionized water) | 0.24 | 0.09 |
| Poly(vinyl alcohol), MW 13,000-23,000; 87-89% hydrolyzed | 2.40 | 0.90 |

An organic solution is prepared by blending 41.7 g of an 11.5 percent solution of Elavacite 2041 PMMA polymer (MW 447,000) in ethyl acetate with 1.6 g of IPBC and 0.7 g acetone. Over a period of fifteen minutes, this solution is introduced directly into an aqueous phase consisting of 100.8 g of deionized water, 19.2 g of a 1.25 percent solution of Kelzan® CC in deionized water, and 2.4 g of polyvinyl alcohol (87-89% hydrolyzed).

The mixture is stirred for 45 minutes at a constant temperature of 50° C. in a double-walled 0.5 liter metal beaker of 8.0 cm diameter equipped with a removable top cover. The stirring is accomplished by means of a VMA-Getzmann Dispermat® with a 6.0 cm dissolver disk/blade; operated at about 900-1500 rpm and a tip speed of 2.8-4.7 m/sec. Minute quantities of Rhodorsil® A416 antifoam is added as necessary. The temperature of the reactor contents is lowered over 30-60 minutes to a temperature of 18-20 degrees C. with continuous stirring. At this temperature, 100 g of deionized water is added at a stirring rate of about 1500 rpm over 10-30 minutes. The microparticles are collected by filtration (e.g. filter bags with 5 microns pore size are used) and dried.

The microparticles are dried for 16 hours at 35° C. and collected. The collected microparticles weigh 4.7 g, which corresponds to a weight recovery of 73 percent based on the weight of the poly(methyl methacrylate) and IPBC ingredients. Up to 27 percent of the microparticles with a particle size of less than 5 microns have not been collected by filtration and remain in the liquid phase. The IPBC content of the collected microparticles is 24.0%, as measured by High Pressure Liquid Chromatography. Their particle size distribution is D5%: 5 microns, D50%: 49 microns, D95%: 106 microns, and D99%: 133 microns.

A delta b-value is recorded and calculated for a test sample of microparticles as being 1.0. By way of comparison, free IPBC under identical test conditions exhibits a delta-b value of about 3.3.

Preparative Example F

Inventive Process for Making Microparticles

The following ingredients are assembled in the following amounts:

| Ingredient | grams | wt % |
|---|---|---|
| Poly(methyl methacrylate) - MW 447,000 | 49.0 | 10.10 |
| Ethyl acetate | 94.09 | 19.39 |
| IPBC crystalline particles (contains >98% IPBC) | 16.3 | 3.36 |
| Acetone (optional) | 3.44 | 0.71 |
| De-ionized water | 320.00 | 65.95 |
| Poly(vinyl alcohol) - MW 13,000-23,000, 87-89% hydrolyzed | 2.40 | 0.49 |

The procedure described above in Preparative Example A is performed in a metal beaker equipped with a removable top cover. The organic liquid phase consists of 49.54 g ethyl acetate, 1.82 g acetone, 1.63 g IPBC, and 4.9 g of PMMA (MW 447,000). The aqueous liquid phase contains 120 g of de-ionized water and 2.40 grams of polyvinyl alcohol that has a molecular mass in the range of 13,000 to 23,000 g/mol and is 87-89% hydrolyzed. The procedure is substantially similar to the procedure described above in Preparative Example A, except that a) higher stirring rates of about 1300 to 1900 rpm are employed; b) while stirring at 50° C., nine two-step additions are carried out, each first step consisting of 1.63 g IPBC dissolved in 4.95 g Ethyl acetate and 0.18 g Acetone and each second step consisting of 4.90 g of solid PMMA (MW 447,000) particles is employed; these additions spaced at equal time intervals over a time period of about 1.5 to 4 hours; c) a defoamer may optionally be added; and d) a UV absorber and/or a HALS may optionally be added.

Example 1

Previously Known Formulations for Comparison

The above-described UV Discoloration Test Procedure is performed with previously known formulations for test periods of four or six hours. In each case, an IPBC use concentration of about 1000 ppm is employed. Delta b values for 4 hours, for six hours, and for eight hours are presented below in Table 1. These results are intended to serve as a benchmarks against which other experimental data may be compared.

TABLE 1

| Test No. | Test Formulation | Invention or Previously Known | delta b for 4 hours | delta b for 6 hours | delta b for 8 hours |
|---|---|---|---|---|---|
| 1 | Stucco[1] | Previously Known | 0.1 | 0.1 | 0.3 |
| 2 | IPBC particles | Previously Known | 3.8 | 4.8 | 5.6 |
| 3 | Melamine formaldehyde-encapsulated IPBC | Previously Known | 3.1 | 4.3 | not recorded |

Legend:
[1]Stolit ® K2 Stucco, commercially available from Sto AG, Germany

Example 2

Microparticles for Stabilizing IPBC

Microcapsules including PMMA are prepared by methods substantially similar to the methods described above in Preparative Examples A, B or C. In each case, an IPBC use concentration of about 1000 ppm is employed. UV Discoloration Test Procedure results for test periods of four or six hours are presented below in Table 2 for microparticles of the invention.

TABLE 2

| Test No. | Test formulation | Invention or Previously Known | weight ratio of IPBC to polymer | delta b for 4 hours | delta b for 6 hours |
|---|---|---|---|---|---|
| 1 | IPBC within or on PMMA (manufactured from IPBC dissolved in organic phase) - Prep. Example C | Invention | 0.33:1 | 0.6 | 0.8 |
| 2 | IPBC within or on PMMA (manufactured from IPBC particles suspended in aqueous phase) - Prep. Example A | Invention | 0.33:1 | 0.7 | 1.0 |
| 3 | IPBC within or on PMMA (manufactured from IPBC particles dispersed in aqueous phase) - Prep. Example B at about 900 rpm | Invention | 0.33:1 | 0.6 | 0.9 |

TABLE 2-continued

| Test No. | Test formulation | Invention or Previously Known | weight ratio of IPBC to polymer | delta b for 4 hours | delta b for 6 hours |
|---|---|---|---|---|---|
| 4 | IPBC within or on PMMA (manufactured from IPBC particles dispersed in aqueous phase) - Prep. Example B at about 2800 rpm | Invention | 0.33:1 | 0.8 | 1.2 |
| 5 | IPBC and UVA within or on PMMA at 0.9:0.1:3 ratio - Prep. Example C | Invention | 0.30:1 | 0.5 | 0.8 |
| 6 | IPBC and UVA II within or on PMMA at 0.9:0.1:3 ratio - Prep. Example C | Invention | 0.30:1 | 0.5 | 0.7 |
| 7 | IPBC and UVA within or on PMMA at 0.9:0.1:9 ratio - Prep. Example C | Invention | 0.10:1 | 0.4 | 0.5 |
| 8 | IPBC and HALS within or on PMMA at 0.9:0.1:3 ratio - Prep. Example B at about 900 rpm | Invention | 0.30:1 | 0.4 | 0.5 |
| 9 | IPBC and HALS within or on PMMA at 0.9:0.1:3 ratio - Prep. Example B at about 2800 rpm | Invention | 0.30:1 | 0.7 | 1.0 |
| 10 | IPBC and HALS within or on PMMA in a 0.9:0.1:9 ratio - Prep. Example A | Invention | 0.10:1 | 0.4 | 0.4 |
| 11 | IPBC and HALS within or on PMMA in a 0.7:0.3:3 ratio - Prep. Example A | Invention | 0.23:1 | 0.4 | 0.5 |
| 12 | IPBC and HALS II within or on PMMA in a 0.9:0.1:3 ratio - Prep. Example C | Invention | 0.30:1 | 0.8 | 1.2 |
| 13 | IPBC and HALS within or on PVAC in a 0.9:0.1:3 ratio - Prep. Example A | Invention | 0.30:1 | 0.7 | 0.9 |
| 14 | IPBC and $TiO_2$ within or on PMMA in a 0.9:0.1:3 ratio - Prep. Example C | Invention | 0.30:1 | 0.7 | 1.0 |
| 15 | IPBC and ZnO within or on PMMA in a 0.9:0.1:3 ratio - Prep. Example C | Invention | 0.30:1 | 0.7 | 0.8 |
| 16 | IPBC within or on Polystyrene - Prep. Example C (only particle fraction 100-200 microns) | Invention | 0.33:1 | 0.8 | not recorded |
| 17 | IPBC within or on Polycarbonate - Prep. Example C (solvent: dichloromethane instead of ethyl acetate; only particle fraction 100-200 microns) | Invention | 0.33:1 | 0.8 | not recorded |
| 18 | IPBC within or on PEMA - Prep. Example C | Invention | 0.33:1 | 1.0 | not recorded |
| 19 | IPBC, UVA III and HALS within or on PMMA in a 0.9:0:05:0.05:3 ratio - Prep. Example C | Invention | 0.30:1 | 0.6 | not recorded |

Legend: PMMA means poly (methyl methacrylate), MW: 350,000.
PVAC means polyvinyl acetate, MW: 500,000.
Polystyrene, MW: 350,000.
Polycarbonate means poly(Bisphenol A carbonate), MW: 28,200.
PEMA means poly (ethyl methacrylate), MW: 515,000.
UVA means 2-(2-Hydroxy-5-methylphenyl)benzotriazole.
UVA II means 2-Hydroxy-4-methoxybenzophenone.
UVA III means 2-(2H-Benzotriazol-2-yl)-4,6-bis(1-methyl-1-phenylethyl)phenol.
HALS means 1,5,8,12-Tetrakis[4,6-bis(N-butyl-N-1,2,2,6,6-pentamethyl-4-piperidylamino)-1,3,5-triazin-2-yl]-1,5,8,12-tetraazadodecane.
HALS II means Poly[[6-[(1,1,3,3-tetramethylbutyl)amino]-s-triazine-2,4-diyl]-[(2,2,6,6-tetramethyl-4-piperidyl)imino]-hexamethylene-[(2,2,6,6-tetramethyl-4-piperidyl)imino].
$TiO_2$ means titanium oxide
ZnO means zinc oxide A comparison of the experimental results above in Tables 2 with those in Table 1 reveals significant improvements in color stability.

Example 3

Microparticles for Stabilizing IPBC

UV Discoloration Test Procedure results for 8 hour test periods are presented below in Table 3 for microparticles of the invention. In each case, an IPBC use concentration of about 1000 ppm is employed. The microcapsules include PMMA and are prepared by methods substantially similar to the methods described above in Preparative Example A, B or C.

TABLE 3

| Test No. | Test Formulation | Invention or Previously Known | weight ratio of IPBC to polymer | delta b for 8 hours |
|---|---|---|---|---|
| 1 | IPBC within or on PMMA | Invention | 0.33:1 | 1.3 |
| 2 | IPBC and UVA within or on PMMA at 0.9:0.1:3 ratio | Invention | 0.30:1 | 1.1 |
| 3 | IPBC and UVA within or on PMMA at 0.9:0.1:9 ratio | Invention | 0.10:1 | 0.5 |
| 4 | IPBC and HALS within or on PMMA at 0.9:0.1:3 ratio | Invention | 0.30:1 | 0.6 |

Legend: UVA means 2-(2-Hydroxy-5-methylphenyl)benzotriazole.
HALS means 1,5,8,12-Tetrakis[4,6-bis(N-butyl-N-1,2,2,6,6-pentamethyl-4-piperidylamino)-1,3,5-triazin-2-yl]-1,5,8,12-tetraazadodecane.

A comparison of the experimental results above in Tables 2 and 3 with those in Table 1 reveals significant improvements in color stability.

Example 4

Effect of Microparticle Size

The above-described UV Discoloration Test Procedure is performed for a test period of four hours with samples of microparticles in different microparticle size ranges. The samples in different size ranges are obtained from a batch of microparticles by screening or filtering. Excepting any microparticle size limitations, the microparticles in the various size ranges are of the invention. In each case, an IPBC use concentration of about 1000 ppm is employed. Delta b values are presented below in Table 4.

TABLE 4

| Test No. | Range of Microparticle Size | delta-b value after 4 hours |
|---|---|---|
| 1 | 1-5 microns | 2.5[2] |
| 2 | 5-20 microns | 1.9[1] |

TABLE 4-continued

| Test No. | Range of Microparticle Size | delta-b value after 4 hours |
|---|---|---|
| 3 | 50-100 microns | 1.6[1] |
| 4 | 100-200 microns | 0.9[2] |
| 5 | 200-300 microns | 0.4[2] |
| 6 | 300-500 microns | 0.3[2] |

Legend:
[1] One PMMA/IPBC sample tested; average value of three UV Discoloration Test Procedure experiments.
[2] Two different PMMA/IPBC samples tested; average value of six UV Discoloration Test Procedure experiments.

Example 5

Effect of Weight Ratio of IPBC to Polymer

The above-described UV Discoloration Test Procedure is performed at an IPBC use level of about 1000 ppm for four hours with samples of microparticles having various weight ratios of IPBC to PMMA polymer. The microparticles include PMMA of 447,000 g/mol molecular mass and have an average particle size of greater than 50 microns. Delta b values are presented below in Table 5a and Table 5b.

TABLE 5a

| Test No. | Weight Ratio of IPBC to PMMA polymer | Wt % IPBC in Microparticles | Wt % Polymer in Microparticles | delta-b for 4 hours |
|---|---|---|---|---|
| 1 | 0.33:1 | 25% | 75% | 1.0 |
| 2 | 9:1 | 90% | 10% | 2.3 |
| 3 | 19:1 | 95% | 5% | 3.4 |

Inspection of Table 5a reveals that microparticles including IPBC and polymer in a weight ratio of 19:1 or greater provide relatively less stabilization for IPBC against discoloration, as compared to similar microparticles having lesser weight ratios. By way of comparison, Table 1 above indicates that IPBC particles with no polymer shielding at all exhibit a delta b of 3.8 for 4 hours, and 4.8 for 6 hours, in the UV Discoloration Test Procedure.

Turning now to Table 5b below, the above-described UV Discoloration Test Procedure is performed at an IPBC use level of about 1000 ppm for four or six hours with samples of microparticles having various weight ratios of IPBC to PMMA polymer and an amount of UV absorber that is about one-ninth by weight of IPBC.

The UV absorber employed is 2-(2-Hydroxy-5-methylphenyl)benzotriazole, commercially available from Sigma-Aldrich Co. LLC, St. Louis, Mo. The microparticles include PMMA of 350,000 and have an average particle size of greater than 50 microns. Delta b values are presented Table 5b.

TABLE 5b

| Test No. | Test Formulation | Wt % IPBC in Microparticles | Wt % Polymer in Microparticles | Weight Ratio of IPBC to Polymer | delta b for 4 hours | delta b for 6 hours |
|---|---|---|---|---|---|---|
| 1 | IPBC and UVA within or on PMMA at 9.0:1.0:90 ratio | 9% | 90% | 0.1:1 | 0.4 | 0.5 |

TABLE 5b-continued

| Test No. | Test Formulation | Wt % IPBC in Microparticles | Wt % Polymer in Microparticles | Weight Ratio of IPBC to Polymer | delta b for 4 hours | delta b for 6 hours |
| --- | --- | --- | --- | --- | --- | --- |
| 2 | IPBC and UVA within or on PMMA at 22.5:2.5:75.0 ratio | 22.5% | 75% | 0.3:1 | 0.5 | 0.8 |
| 3 | IPBC and UVA within or on PMMA at 27:3.0:70 ratio | 27.0% | 70% | 0.38:1 | 0.8 | 0.9 |
| 4 | IPBC and UVA within or on PMMA at 31.5:3.5:65 ratio | 31.5% | 65% | 0.48:1 | 0.8 | 1.2 |
| 5 | IPBC and UVA within or on PMMA at 36:4.0:60 ratio | 36.0% | 60% | 0.6:1 | 1.2 | 1.4 |
| 6 | IPBC and UVA within or on PMMA at 40.5:4.5:55 ratio | 40.5% | 55% | 0.74:1 | 1.3 | 1.8 |
| 7 | IPBC and UVA within or on PMMA at 45:5.0:50 ratio | 45.0% | 50% | 0.9:1 | 1.4 | 1.9 |
| 8 | IPBC and UVA within or on PMMA at 54:6.0:40 ratio | 54.0% | 40% | 1.35:1 | 1.5 | 1.9 |
| 9 | IPBC and UVA within or on PMMA at 58.5:6.5:35 ratio | 58.5% | 35% | 1.67:1 | 1.9 | 2.7 |
| 10 | IPBC and UVA within or on PMMA at 63:7.0:30 ratio | 63.0% | 30% | 2.1:1 | 2.0 | 2.7 |

Inspection of Table 5b reveals that microparticles including IPBC and UVA exhibit stabilization for IPBC against discoloration that is inversely proportional to their weight ration of IPBC to polymer.

The above Examples are intended to better communicate the invention, and do not limit the invention in any way. The invention is defined solely by the appended claims.

What is claimed is:

1. Microparticles for stabilizing 3-iodo-2-propynyl butylcarbamate against discoloration, which comprise:
   a polymer that absorbs light over a range of ultraviolet wavelengths associated with 3-iodo-2-propynyl butylcarbamate discoloration by sunlight and other ultraviolet light sources; and
   a biocidal composition including 3-iodo-2-propynyl butylcarbamate and optionally, an additional biocidal material;
   which microparticles stabilize 3-iodo-2-propynyl butylcarbamate against discoloration by sunlight and other ultraviolet light sources, and have a particle size in the range of more than 20 to about 1000 microns and a surface area in the range of about 0.001 to about 0.9 m2 per gram.

2. The microparticles of claim 1, in which the polymer has an absorbance that is 0.03 or greater at all wavelengths in the range of about 290 to about 380 nanometers.

3. The microparticles of claim 2, in which the polymer has an absorbance that is 0.03 or greater at all wavelengths in the range of about 295 to about 320 nanometers.

4. The microparticles of claim 1, in which the polymer is selected from the group consisting of poly(methyl methacrylate), poly(ethyl methacrylate), polyvinyl acetate, polystyrene, polycarbonate, and copolymers thereof.

5. The microparticles of claim 1, in which the polymer is selected from the group of consisting of poly(methyl methacrylate), poly(ethyl methacrylate), polyvinyl acetate, polystyrene, polycarbonate, and mixtures thereof.

6. The microparticles of claim 1, in which the polymer is selected from the group consisting of poly(methyl methacrylate), poly(ethyl methacrylate), and mixtures thereof.

7. The microparticles of claim 1, in which the weight ratio of 3-iodo-2-propynyl butylcarbamate to the polymer is in the range of about 0.01:1 to about 9:1.

8. The microparticles of claim 1, in which the weight ratio of 3-iodo-2-propynyl butylcarbamate to the polymer is in the range of about 0.1:1 to about 2:1.

9. The microparticles of claim 1, in which the weight ratio of 3-iodo-2-propynyl butylcarbamate to the polymer is in the range of about 0.2:1 to about 11.

10. The microparticles of claim 1, which are dispersed in a liquid carrier phase.

11. The microparticles of claim 1 which include one more additional biocides.

12. The microparticles of claim 11, in which the additional biocide is selected from the group consisting of isoproturon, Terbutryn, 3 (3,4-dichlorophenyl)-1,1-dimethylurea; N-cyclopropyl-N'-(1,1-dimethylethyl)-6-(methylthio)-1,3,5-triazine-2,4-diamine; carbendazim; zinc pyrithione, 4,5-dichloro-2-n-octyl-3-isothiazolone, 2-n-octyl-4-isothiazolin-3-one, and mixtures thereof.

13. The microparticles of claim 11, in which the additional biocide is isoproturon.

14. The microparticles of claim 11, in which the additional biocide is Terbutryn.

15. The microparticles of claim 1, in which the polymer has a molecular mass in the range of about 15,000 to about 1,000,000 g/mol.

16. The microparticles of claim 1, in which the polymer is poly(methyl methacrylate) and has a molecular mass in the range of about 40,000 to about 700,000 g/mol.

17. The microparticles of claim 1, which include a free radical scavenger and/or an ultra-violet absorber.

18. The microparticles of claim 17, in which the biocidal composition includes the free radical scavenger, and the free radical scavenger is a hindered amine light stabilizer.

19. The microparticles of claim 18, in which the weight ratio of 3-iodo-2-propynyl butylcarbamate to the free radical scavenger is in the range of about 19:1 to about 2.3:1.

20. The microparticles of claim 17, in which the biocidal composition includes the ultra-violet absorber, and the ultra-violet absorber is a benzotriazole or a benzophenone.

21. The microparticles of claim 20, in which the weight ratio of 3-iodo-2-propynyl butylcarbamate to the ultra-violet absorber is in the range of about 19:1 to about 2.3:1.

22. The microparticles of claim 17, in which the weight ratio of polymeric material to the biocidal composition is in the range of about 9:1 to about 1:9.

23. The microparticles of claim 1, which have a particle size in the range of more than 30 to about 800 microns.

24. The microparticles of claim 1, which have a particle size in the range of more than 40 to about 500 microns.

25. The microparticles of claim 1, which have a particle size in the range of more than 50 to about 100 microns.

26. The microparticles of claim 1, in which the polymer exhibits absorbance of less than 0.10 at all wavelengths in the range of about 400 to about 740 nanometers.

27. The microparticles of claim 1, in which the polymer exhibits absorbance of less than 0.05 at all wavelengths in the range of about 400 to about 740 nanometers.

28. The microparticles of claim 1, in which the polymer appears colorless to the human eye.

* * * * *